US00PP37223P2

(12) United States Plant Patent
Bak

(10) Patent No.: US PP37,223 P2
(45) Date of Patent: Jan. 20, 2026

(54) ***TILLANDSIA* PLANT NAMED 'PREZIOSA'**

(50) Latin Name: *Tillandsia sp.*
Varietal Denomination: PREZIOSA

(71) Applicant: Corn Bak BV, Assendelft (NL)

(72) Inventor: Elly Bak, Rijsenhout (NL)

(73) Assignee: Corn Bak B.V. (NL)

( * ) Notice: Subject to any disclaimer, the term of this patent is extended or adjusted under 35 U.S.C. 154(b) by 0 days.

(21) Appl. No.: 19/185,512

(22) Filed: Apr. 22, 2025

(51) Int. Cl.
*A01H 5/12* (2018.01)
*A01H 6/22* (2018.01)

(52) U.S. Cl.
USPC ..... Plt./370

(58) Field of Classification Search
USPC ..... Plt./370
See application file for complete search history.

*Primary Examiner* — Susan Mccormick Ewoldt

(57) ABSTRACT

A new and distinct cultivar of *Tillandsia* plant named PREZIOSA is disclosed, characterized by solid growth habit, funnel-form rosette plant, measuring about 30 cm in height (above the pot when flowering); numerous green colored foliage, measuring about 40 cm in length and about 3 cm in width; superior floral bract production; bracts have unique red-purple inflorescence; and long-lasting habit. The new variety is a *Tillandsia*, typically produced as an ornamental plant.

1 Drawing Sheet

Latin name of the genus and species: *Tillandsia sp.*
Variety denomination: 'PREZIOSA'.

BACKGROUND OF THE INVENTION

The present invention relates to a new and distinct cultivar of *Tillandsia* plant, botanically known as *Tillandsia* sp., of the family *Bromeliaceae*, and hereafter referred to as 'PREZIOSA'.

The new *Tillandsia* 'PREZIOSA' originated from a cross made in a controlled breeding program by the inventors in 2003. The seed parent is the unnamed and unpatented *Tillandsia* selection identified by code '0307150001'. The pollen parent is the unnamed and unpatented *Tillandsia* selection identified by code '0307150005'. The new *Tillandsia* was discovered and selected by the inventors in 2008 as a single flowering plant within the progeny of the stated cross in a controlled environment in Assendelft, The Netherlands.

Asexual reproduction of the new cultivar 'PREZIOSA' was first performed by off-shoots beginning in 2008 in Assendelft, the Netherlands, and then by tissue culture beginning in 2018 in Assendelft, The Netherlands. The new cultivar reproduces true to type.

Methods for cultivation and crossing of *Tillandsia* are well known. For a detailed discussion, reference is made to the following publications, which are incorporated herein by reference: Benzig, David H., THE BIOLOGY OF THE BROMELIADS, Mad River Press, Inc., Eureka (1980); Zimmer, Karl, BROMELEIN, Verlag, Paul Parey, Berlin (1986); and Rauh, Werner, BROMELEIN, Verlag Eugen Ulmer, Stuttgart (1981).

SUMMARY OF THE INVENTION

The following traits have been repeatedly observed and are determined to be the unique characteristics of 'PREZIOSA', which in combination distinguish 'PREZIOSA' as a new and distinct *Tillandsia* cultivar:

1. Solid growth habit, plants are both strong and healthy.
2. Funnel-form rosette plant, measuring about 30 cm in height (above the pot when flowering).
3. Numerous, green colored foliage, measuring about 40 cm in length and 3 cm in width.
4. Erect panicle with side branches, red-purple inflorescence.
5. Long-lasting habit.

PARENT COMPARISONS

Plants of the parent cultivars are no longer available to provide a botanical comparison with the new *Tillandsia* hybrid 'PREZIOSA'. The breeder has neither records nor plants of the parent varieties.

COMMERCIAL COMPARISON

Plants of *Tillandsia* 'PREZIOSA' are similar in some horticultural characteristics to the variety *Tillandsia* 'Spirit', unpatented. The new variety, however, differs in the following:

1. Plants of the new variety are larger than plants of this comparator. Plants of 'Spirit' are suitable for 8 and 8 cm pots, plants of 'PREZIOSA' are suitable for 12 to 15 cm pots.
2. Bract color of the new variety is red-purple, while the bract color of this comparator is red.

BRIEF DESCRIPTION OF THE PHOTOGRAPH

The accompanying photograph illustrates the overall appearance of the new *Tillandsia* cultivar 'PREZIOSA' showing the colors as true as is reasonably possible with colored reproductions of this type. Colors in the photograph may differ slightly from the color values cited in the detailed botanical description which accurately describes the color of 'PREZIOSA'. The accompanying figure shows a side perspective view of a typical potted flowering plant of 'PREZIOSA' at about 15 months of age from potting.

DETAILED BOTANICAL DESCRIPTION

'PREZIOSA' has not been tested and observed under all possible environmental conditions. The phenotype of the new cultivar may vary with variations in environment such as temperature, light intensity, frequency of fertilization, composition of fertilizer, flowering treatment, day length and humidity, without any change in the genotype of the plant. For example, substantial differences in plant height and diameter, number of leaves, can result depending on the size of the plant at the time that flowering is induced by flowering treatment. Since treatment to induce flowering disrupts normal watering and fertilization regimens, flowering treatment of relatively smaller plants adversely affects the growth of the plant.

The aforementioned photograph, together with the following observations, measurements and values describe the new Tillandsia 'PREZIOSA' as grown in a greenhouse in Assendelft, The Netherlands, under conditions which closely approximate those generally used in commercial practice. Plants of 'PREZIOSA' were grown in a greenhouse with day temperatures ranging from 20° C. to 28° C. and night temperatures ranging from 18° C. to 23° C. No artificial lighting or photoperiodic treatments were conducted, but plants of 'PREZIOSA' are forced into flowering. The following fertilizer is added when growing plants of 'PREZIOSA': 1 part nitrogen, 0.6 parts phosphor, 2 parts Kalium and 0.1 parts magnesium.

Color references are made to the Royal Horticultural Society Colour Chart (RHS), 2001 edition, except where general colors of ordinary significance are used. Color values were taken under daylight conditions in a greenhouse in Assendelft, The Netherlands. The age of the plants of 'PREZIOSA' described is about 13 weeks after flowering treatment.

Botanical classification: *Tillandsia* sp. 'PREZIOSA'.

PROPAGATION

Propagation Method: Tissue culture.

PLANT

General Appearance and Form:
- *Shape*.—Funnel-form rosette.
- *Height*.—About 30 cm when flowering.
- *Width*.—About 55 cm.

Growth Habit: Stemless.
Plant Vigor: Good.
Flowering Season: A fully grown plant can flower year-round, starting about 13 weeks after induction of natural light or through flowering treatment.
Cold Tolerance: Frost tender. Temperatures below 5° C. may damage plants.
Fragrance: None.

FOLIAGE

Leaf:
- *Quantity*.—About 18, depending on the size of the plant.
- *Average Length*.—40 cm when flowering.
- *Average Width*.—3 cm.
- *Overall shape*.—Linear.
- *Blade shape*.—Narrowly triangular.
- *Apex*.—Cuspidate.
- *Base*.—Strap-like around central axis.
- *Margin*.13 Entire.
- *Texture*.—Coarse lepidote, both sides.
- *Aspect*.—Overall curved.
- *Color* (*varies somewhat depending on growing conditions*).—Mature and Immature, Upper Side: RHS Green 137A. Mature and Immature, Under Side: RHS Green 137B tinged 144A.

INFLORESCENCE

Flowers are mostly disposed within the floral bracts and rarely open full.
- *Borne*.—Erect stalks.
- *Type*.—Compound (branching).
- *Length*.—About 40 cm.
- *Diameter*.—About 18 cm.
- *Flowers per Inflorescence*.—Average 115 true flowers within inflorescence.
- *Color*.—Near RHS Red-Purple 58B.

Petals:
- *Quantity*.—3 per flower.
- *Length*.—About 3.8 cm.
- *Width*.—About 0.7 cm.
- *Shape*.—Ligulate.
- *Apex*.—Obtuse.
- *Base*.—Fused.
- *Color*.—Upper Surface: Near RHS Violet-Blue 83A. Under Surface: Near RHS Violet-Blue 83A.

Sepals:
- *Quantity*.—3 per flower.
- *Length*.—About 2.5 cm.
- *Width*.—About 0.8 cm.
- *Shape*.—Ligulate.
- *Apex*.—Acute.
- *Base*.—Fused.
- *Color*.—Near RHS White 158C, apex near Red-Purple 58C.

Scape:
- *Number*.—1.
- *Length*.—About 20 cm.
- *Width*.—About 1 cm.
- *Scape Bracts*.—Quantity: About 8. Arrangement: Alternate. Length: Average 25 cm. Width: 1.5 cm. Shape: Linear. Apex: Acuminate. Base: Fused. Margin: Entire. Texture: Smooth. Color, Upper and Under Surfaces: Near RHS Green 137B.

Primary Bracts:
- *Quantity*.—About 8.
- *Arrangement*.—Alternate.
- *Length*.—4.5 to 11.5 cm.
- *Width*.—About 2 cm.
- *Shape*.—Lanceolate, tips curved downwards.
- *Apex*.—Obtuse to acute.
- *Base*.—Fused.
- *Margin*.—Entire.
- *Texture*.—Smooth.
- *Color, Upper and Under Surfaces*.—Near RHS Red-Purple 58C.

Branches:
- *Quantity*.—About 8.
- *Length*.—About 9 cm.

*Diameter*.—About 1.5 cm.
*Color, Upper and Under Surfaces*.—Near RHS Red-Purple 58C.

Floral Bracts:
*Quantity*.—About 100.
*Length*.—About 3 cm.
*Diameter*.—About 1.5 cm.
*Shape*.—Lanceolate.
*Apex*.—Acute.
*Base*.—Fused.
*Margin*.—Entire.
*Texture*.—Smooth.
*Color, Upper and Under Surfaces*.—Near RHS Red-Purple 58C.

REPRODUCTIVE ORGANS

Androecium:
*Stamen*.—Number: 6 per flower. Length: About 0.5 cm. Diameter: About 0.1 mm. Color: Near RHS White 155D.
*Anther*.—Shape: Linear. Length: About 0.5 cm. Color: RHS Yellow 7C. Pollen: Moderate. Pollen Color: RHS Yellow 7D.

Gynoecium:
*Stigma*.—Shape: 3-parted. Width: About 0.2 cm. Color: RHS Green 143D
*Style*.—Length: About 4 cm. Color: White; too small to qualify RHS value.
*Ovary*.—Position: Superior. Shape: Conical. Length: About 0.6 cm. Diameter: About 0.4 cm.

OTHER CHARACTERISTICS

Seeds: Not observed.
Fruit: Not observed.
Disease/pest resistance: No resistance nor susceptibility to normal diseases and pests of *Tillandsia* have been observed.

What is claimed is:

1. A new and distinct cultivar of *Tillandsia* plant named PREZIOSA as herein illustrated and described.

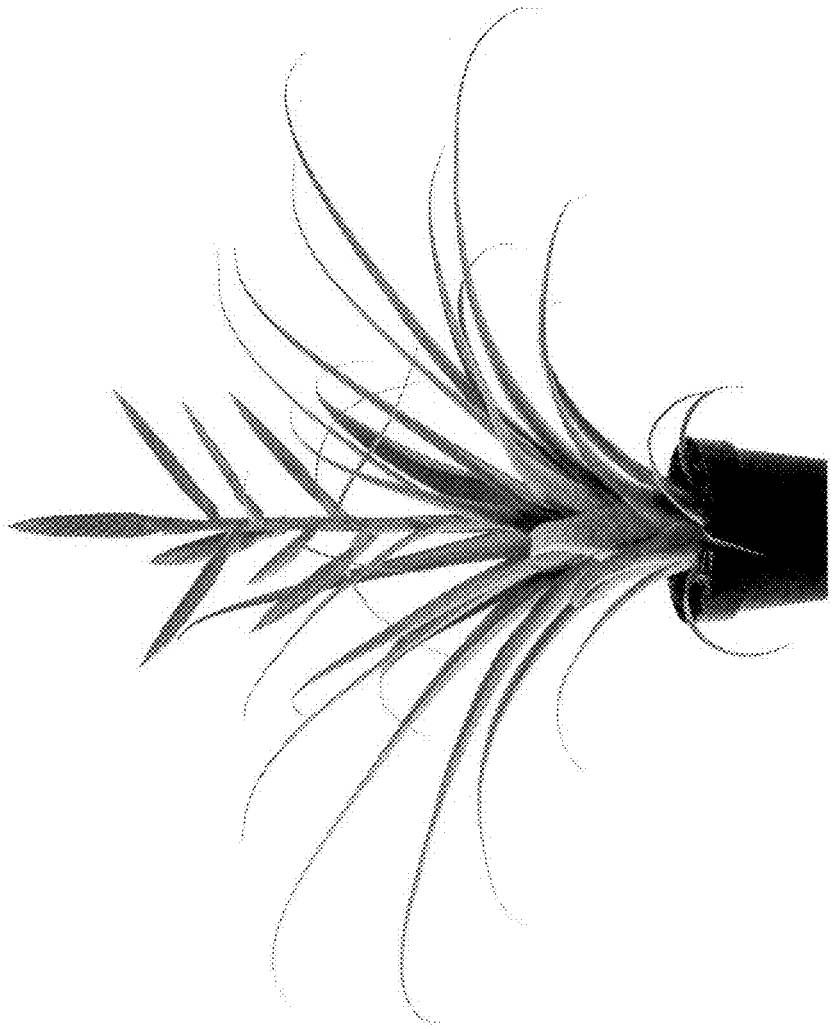

* * * * *